US010408731B2

(12) United States Patent
Pedalino et al.

(10) Patent No.: US 10,408,731 B2
(45) Date of Patent: Sep. 10, 2019

(54) HIGH EFFICIENCY PARTICULATE AIR FILTER TEST SYSTEM AND METHOD

(71) Applicants: Dean A. Pedalino, Clearwater, FL (US); Peter L. Day, Coral Springs, FL (US); John R. Bentley, II, Winter Haven, FL (US)

(72) Inventors: Dean A. Pedalino, Clearwater, FL (US); Peter L. Day, Coral Springs, FL (US); John R. Bentley, II, Winter Haven, FL (US)

(73) Assignee: Performance Assurance Systems LLC, Clearwater, FL (US)

( * ) Notice: Subject to any disclaimer, the term of this patent is extended or adjusted under 35 U.S.C. 154(b) by 0 days.

(21) Appl. No.: 16/167,186

(22) Filed: Oct. 22, 2018

(65) Prior Publication Data

US 2019/0056301 A1 Feb. 21, 2019

Related U.S. Application Data

(63) Continuation-in-part of application No. 15/241,825, filed on Aug. 19, 2016.

(51) Int. Cl.
*G01N 15/08* (2006.01)
*F24F 3/16* (2006.01)
*F24F 13/28* (2006.01)

(52) U.S. Cl.
CPC .......... *G01N 15/08* (2013.01); *F24F 3/1603* (2013.01); *B01D 2273/18* (2013.01); *F24F 13/28* (2013.01); *G01N 2015/084* (2013.01)

(58) Field of Classification Search
None
See application file for complete search history.

(56) References Cited

U.S. PATENT DOCUMENTS 2,322,168 A * 6/1943 Smith ............... F16L 37/113
251/149.6
4,110,552 A * 8/1978 Lombardi ............ H05K 9/0007
174/353

(Continued)

OTHER PUBLICATIONS

Pharmaseal FFU: Room Side Testable Fan/Filter Ceiling Module. [online]. date accessed: Mar. 18, 2019. https://www.camfil.us/FileArchive/_30_Product_Support_Material_CamTab/Product%Literature/Clean%20Room%20Filters%20and%20Modules/Pharmaseal%20FFU%20Room%20Side%20Testable%20Fan%20Filter%20Ceiling%20Module%20Product%20Sheet.pdf.

*Primary Examiner* — Paul M. West
*Assistant Examiner* — Mark A Shabman
(74) *Attorney, Agent, or Firm* — Smith & Hopen, P.A.; Paul Murty

(57) ABSTRACT

A system and method for accurately and efficiently testing a HEPA filter in a sterile environment, such as a clean room, by creating a closed-loop system. The system includes a multi-port interface including at least a challenge port and a verification port, each port being in communication with an area upstream from the HEPA filter. Through the challenge port, test substances are introduced to a supply air duct that is in communication with a HEPA filter. Through the verification port, a concentration of the test substances can be measured for comparison with a concentration that passed through the HEPA filter, i.e. downstream from the HEPA filter. As such, test substances can be dispersed throughout the air conditioning system before interacting with the HEPA filter, and accurately measured. The closed loop between the ports provides an accurate measurement of the concentration of test substances to test the HEPA filter.

10 Claims, 17 Drawing Sheets

(56) References Cited

U.S. PATENT DOCUMENTS

| | | | | |
|---|---|---|---|---|
| 4,494,403 A | * | 1/1985 | Bowers | B01D 46/0006 73/40.7 |
| 2006/0276120 A1 | * | 12/2006 | Cherry, Sr. | F24F 13/28 454/56 |
| 2012/0305094 A1 | * | 12/2012 | Wallace | B01D 46/0004 137/15.01 |

* cited by examiner

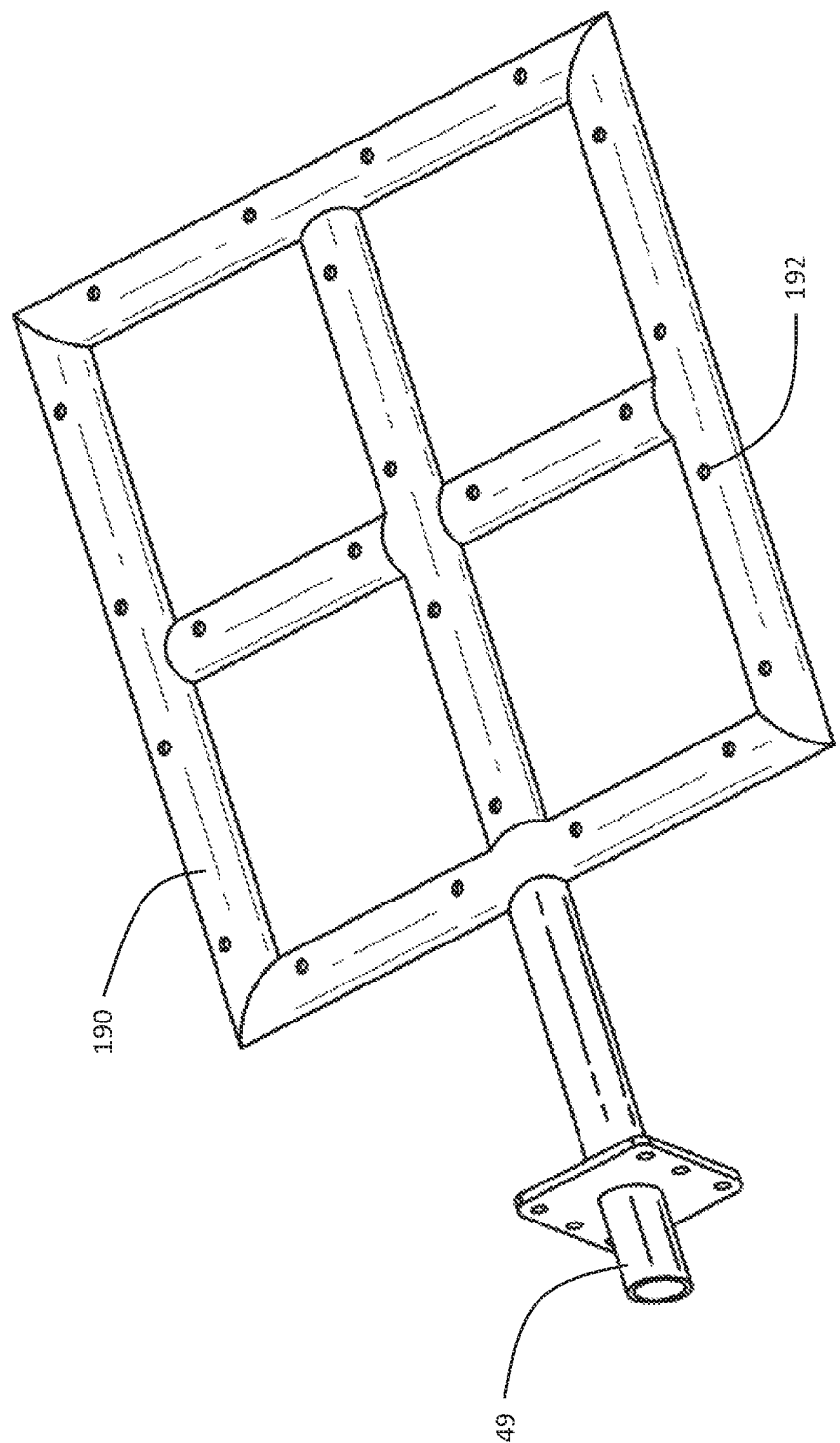

HIGH EFFICIENCY PARTICULATE AIR FILTER TEST SYSTEM AND METHOD

CROSS-REFERENCE TO RELATED APPLICATIONS

This nonprovisional application is a continuation-in-part of and claims priority to nonprovisional application Ser. No. 15/241,825, entitled "Filter Test System," filed Aug. 19, 2016 by the same inventors.

BACKGROUND OF THE INVENTION

1. Field of the Invention

This invention relates, generally, to high efficiency particulate air (HEPA) filter test systems. More specifically, it relates to a multi-port system including a challenge port and a verification port, the multi-port system being in communication with a HEPA filter, thereby allowing a technician to easily and efficiently test the HEPA filter via the multi-port system without the need to open the ceiling of a sterile room during testing, and with reduced risk of contamination to the sterile room during testing.

2. Brief Description of the Prior Art

Sterile rooms often include high-efficiency filters, such as HEPA filters, designed to remove virtually all airborne particles and/or contaminants from the sterile room to prevent contamination, disease, and infection. HEPA filters can trap and contain fine particles in the air, making them ideal for use in sterile environments, such as pharmaceutical laboratories and medical clinics, as well as environments in which clean air is desirable, such as aircrafts and electronics that utilize recirculated air. Particularly in sterile environments, HEPA filters require frequent testing to ensure that the filters are in functioning condition and are removing at least a minimum amount of air particles from the ambient air in the environment to meet ISO standard. Typical testing methods include creating a hole in a HEPA filter, just upstream of the filter media, to introduce a testing substance slightly upstream of the filter, such as via an aerosol. A hood or other containment device surrounds the HEPA filter, such that the air traveling through the HEPA filter is contained within a specific area. Finally, a technician is located downstream of the filter, such as within a sterile room, and the technician uses a device to capture air escaping the filter and detecting the presence of the testing substance that travels through the filter and into the sterile room.

While such a method can be effective at detecting leaks within the filter, the testing method is highly inaccurate because there is no way to verify the amount of testing substance within the system, and particularly there is no way to verify the mixture of testing substance within the air of the system. For example, if the testing substance is introduced into the air flow just above the filter media, it is unlikely that the testing substance will sufficiently disperse within the air to provide an accurate testing result. Moreover, typical systems do not include multiple testing ports in a closed loop with a HEPA filter, meaning that there is no way to ensure an accurate comparison between air just upstream of the filter with air just downstream of the filter.

For HEPA filter testing in particular, it is essential to read accurate results during testing, since the concentration of contaminants measured determines the need to replace the HEPA filter. If the results are inaccurate, a HEPA filter may be prematurely replaced if the test incorrectly yields higher values, making testing and replacement costly due to the early replacement; alternatively, replacement of the HEPA filter may be delayed if the test incorrectly yields lower values, potentially leading to contamination of the room, as well as the people working in the room, equipment housed in the room, and substances in the room.

Accordingly, what is needed is an easily-accessible filter testing system and method of use that creates a closed-loop with the filter to provide accurate testing results in an efficient manner. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for an efficient and accurate system for testing a high efficiency particulate air filter with a reduced risk of introducing contaminants to a sterile environment is now met by a new, useful, and nonobvious invention.

The novel system includes a multi-port interface including a challenge port and a verification port, the multi-port interface in communication with a high efficiency particulate air (HEPA) filter. Challenge substances are introduced upstream from the HEPA filter via the challenge port, and the HEPA filter is tested by detecting a concentration of the challenge substance passing through the HEPA filter by a technician or machine disposed downstream from the HEPA filter. The challenge port is in communication with a duct, such as a supply air duct, disposed upstream from the high efficiency particulate air filter, such that the challenge substance is dispersed throughout the supply air duct and mixed with the gases already present in the unit prior to passing through the HEPA filter. The verification port is disposed just upstream from at least a portion of the high efficiency particulate air filter, such that the verification port is designed to detect an amount of the challenge substance disposed within the air inside the system just prior to encountering the HEPA filter. As such, if there is a leak in the system (i.e., if a technician detects a higher than expected concentration of the challenge substance downstream of the HEPA filter as compared with the concentration measured via the verification port), the technician can accurately determine the amount and location of the leak by comparing the upstream and downstream concentrations of the challenge substance. If the concentration of the challenge substance detected via the technician is greater than the concentration measured via the verification port by more than a threshold value, the high efficiency particulate air filter includes a leak and should be replaced to prevent contamination of the sterile room downstream from the HEPA filter.

In an embodiment of the system, the challenge port includes a valve extending toward the aperture of the challenge port, with the valve being adapted to control the flow of the challenge substance through the challenge port. The default configuration of the system is closed, such that air does not flow through the system—as such, the valve must be translated and actuated to allow for air to flow through the system during testing. Similarly, the verification port includes a valve extending toward the aperture of the verification port, with the valve being adapted to control the flow of air through the verification port.

An embodiment of the system includes a dispersal pipe coupled to the challenge port and disposed within the area upstream from the HEPA filter. The dispersal pipe is adapted to disperse the challenge substance throughout the area to mix the challenge substance with the air within the area. The dispersal pipe includes a plurality of apertures designed to evenly disperse the challenge substance within the area of the duct disposed upstream from the HEPA filter. A collective diameter of the plurality of apertures is equal to a diameter of the first intermediate line, thereby reducing a risk of impaction associated with differences in pressure.

The multi-port interface includes a cam screw in communication with one or more of the challenge port and the verification port. The cam screw is adapted to apply a force against a spring-loaded component of at least one of the ports to compress the spring, allowing a line to be inserted and removed from the port. In a locked configuration, the cam screw does not apply any force against either spring, and the input/output lines cannot be safely removed from the multi-port interface. In an unlocked configuration, the cam screw applies the force against one or more of the springs to allow for the safe removal of the input/output lines.

A novel method is also presented for testing a HEPA filter. The method includes the steps of injecting the challenge substance through the challenge port; dispersing the challenge substance into the area upstream from the HEPA filter; removing an amount of air in the area upstream from the HEPA filter via the verification port; measuring the concentration of the challenge substance in the air removed from the system, measuring the concentration of the challenge substance immediately downstream from the HEPA filter; and comparing the measured concentrations to determine if there is a leak in the HEPA filter. If the concentration of the challenge substance measured downstream from the HEPA filter is above a threshold value, the HEPA filter likely includes a leak and should be replaced.

An object of the invention is to provide an apparatus including multiple ports in communication with a HEPA filter, such that the HEPA filter can be easily, efficiently, and accurately tested without the need to physically access a space above a sterile room, such as by removing ceiling panels or otherwise gaining physical access to the HEPA filter.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which:

FIG. 12B is a perspective view of an embodiment of a dispersal pipe adapted to be disposed within a HEPA filter, in accordance with an embodiment of the present invention.

DETAILED DESCRIPTION OF THE INVENTION

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a," "an," and "the" include plural referents unless the content clearly dictates otherwise. As used in this specification and the appended claims, the term "or" is generally employed in its sense including "and/or" unless the context clearly dictates otherwise.

The present invention includes a system and method for accurately, efficiently, and safely testing a HEPA filter without introducing contaminants into a sterile environment by creating a closed-loop testing system. The system includes a multi-port interface including a challenge port for introducing a test substance to the filter, and a verification port through which contaminants in the filter can be accurately measured. Moreover, the system is a closed-loop testing system because both the challenge port and the verification port are in communication with the filter, such that the substance introduced via the challenge port flows toward the filter and can be measured via the verification port prior to interacting with the HEPA filter. As such, the system provides an accurate measurement of the amount of testing substance within the system just upstream of the HEPA filter, where the verification port is coupled to provide the accurate measurement, which can then be compared to the test results measured by a technician located downstream of the HEPA filter.

Figure 1:
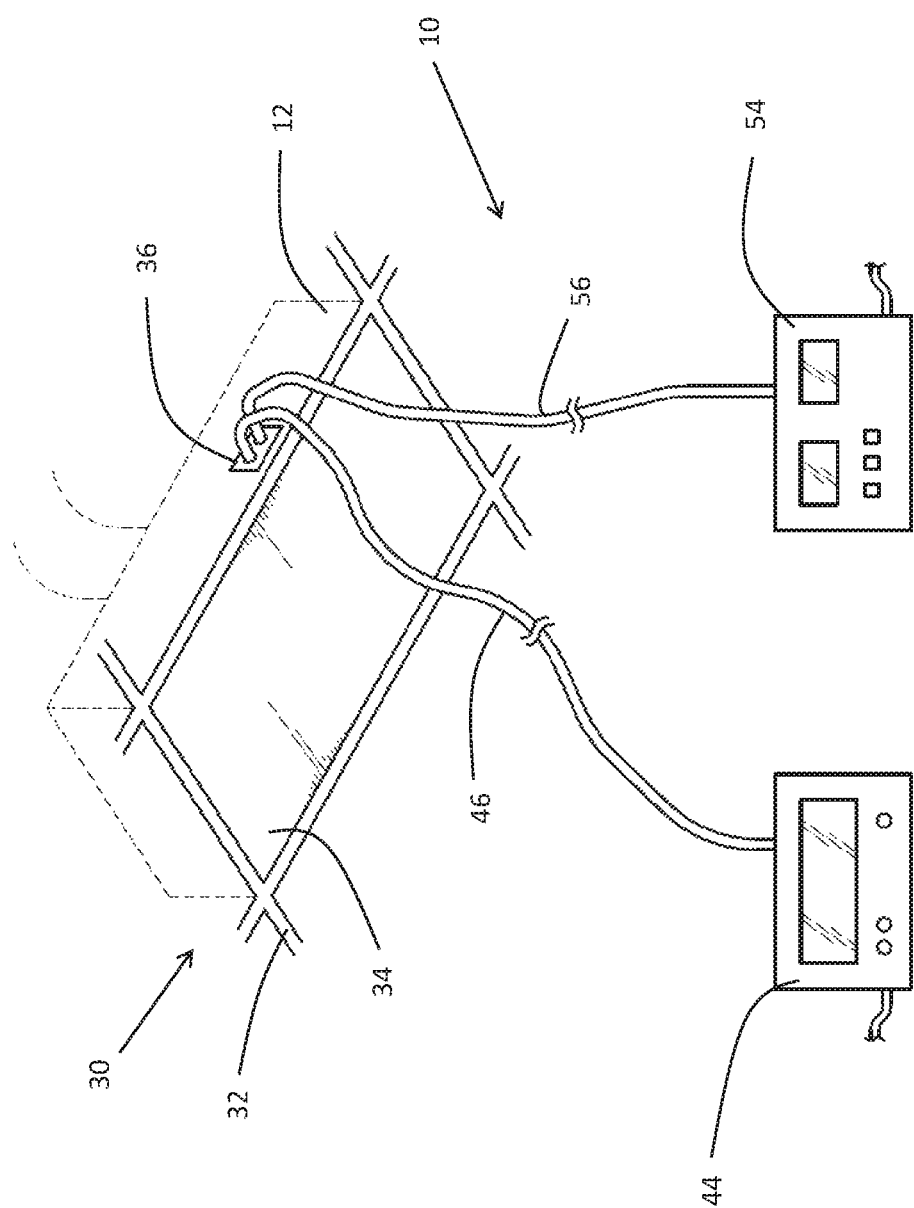
FIG. 1 is a perspective view of a filter test system, including a multi-port system disposed within a ceiling of a sterile room and in communication with a HEPA filter, in accordance with an embodiment of the present invention.

As shown in FIG. 1, an embodiment of system 10 includes multi-port interface 36 in communication with HEPA filter 12, challenge equipment 44, and verification equipment 54. Multi-port interface 36 is disposed in ceiling 30, which includes a plurality of panels 34 connected by a plurality of frames 32. Similarly, HEPA filter 12 is disposed within ceiling 30 and is typically coupled to a duct through which air is either injected into the room underneath ceiling 30, or removed from the room. In an embodiment, challenge equipment 44 and verification equipment 54 are disposed within the room underneath ceiling 30, such that one or more technicians can easily access the equipment without the need to dismantle any of the components of HEPA filter 12 or ceiling 30, such as panels 34 or frame 32.

Still referring to FIG. 1, the equipment 44, 54 and HEPA filter 12 form a closed-loop through multi-port interface 36, with challenge equipment 44 in communication with multi-port interface 36 via input line 46, and verification equipment 54 in communication with multi-port interface 36 via output line 56. Due to the closed nature of system 10, substances may enter HEPA filter 12 from challenge equipment 44 via input line 46, and exit HEPA filter 12 to verification equipment 54 via output line 56. As such, system 10 prevents the escape of any substances introduced to system 10 via challenge equipment 44. Instead, the substances from challenge equipment 44 are either retained by HEPA filter 12, or flow to verification equipment 54, without entering the room in which system 10 is utilized, which is typically a sterile room. The closed-loop system will be discussed in greater detail below.

Figure 2:
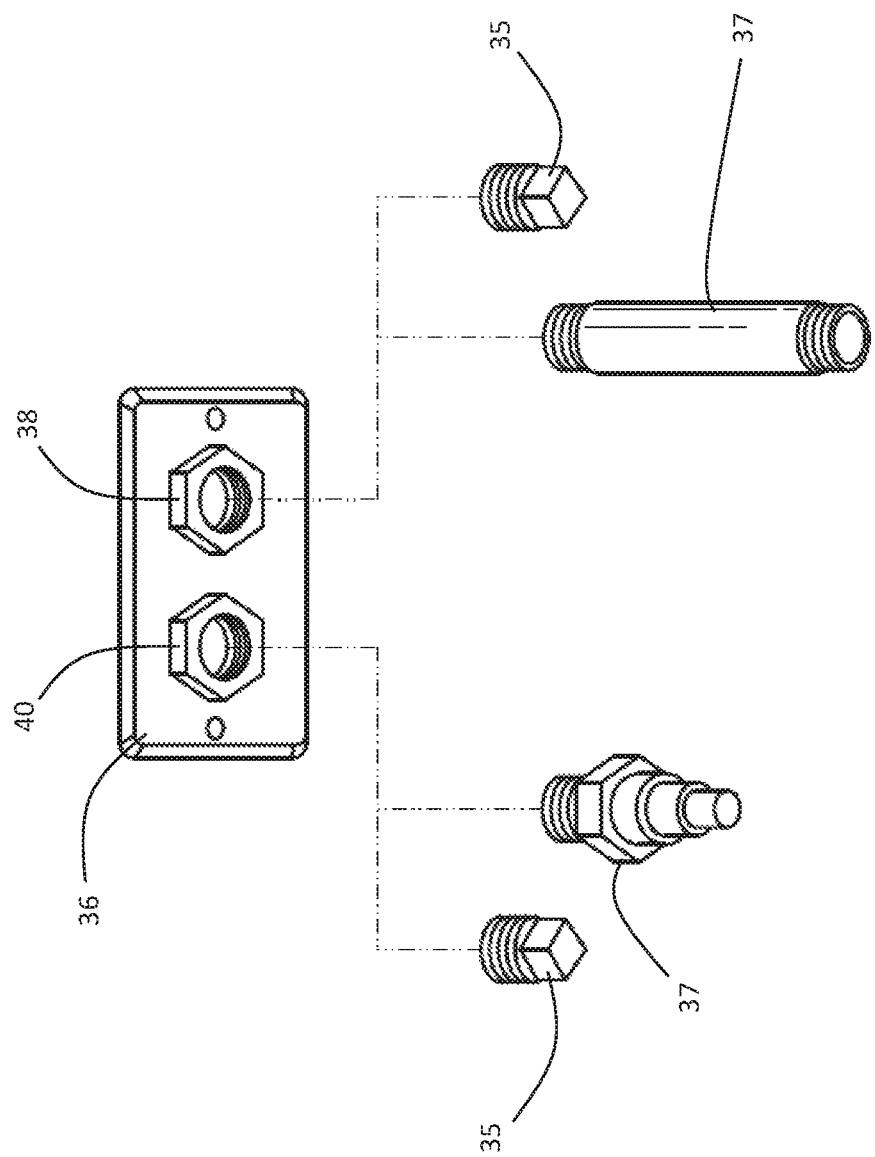
FIG. 2 is a close-up perspective view of the multi-port system of FIG. 1, including a challenge port and a verification port, in accordance with an embodiment of the present invention.

Referring now to FIG. 2, multi-port interface 36 includes a plurality of ports, thereby creating a channel through which a technician can interact with HEPA filter 12. Multi-port interface 36 includes at least challenge port 38 and verification port 40, each of which is in communication with HEPA filter 12, thereby providing access to and from filter 12 via multi-port interface 36. For example, input line 46 can be secured to challenge port 38, thereby indirectly coupling challenge equipment 44 with multi-port interface 36. Similarly, output line 56 can be secured to verification port 40, thereby coupling verification equipment 54 with multi-port interface 36. As such, multi-port interface 36 provides a simple interface for the input and the output of testing substances designed to accurately test the condition of HEPA filter 12 without the need for a complex, time-intensive, or costly testing apparatus or method.

Each of the ports on multi-port interface 36 includes a stopper 35 and a connector 37, each of which is designed to control the flow of particles through multi-port interface 36 to and from HEPA filter 12. For example, challenge port 38 includes input connector 48 and input stopper 60, with input connector 48 providing an attachment point for challenge equipment 44. In addition, input stopper 60 is disposed within challenge port 38 and is in communication with input connector 48, such that input stopper 60 controls the flow of substances through challenge port 38 toward HEPA filter 12. Similarly, verification port 40 includes output connector 58 and output stopper 50, with output connector 58 providing an attachment point for verification equipment 54. In addition, output stopper 50, similar to input stopper 50, is in communication with output connector 58. As such, output stopper 50 controls the flow of substances (such as gas or contaminants, if leaking through HEPA filter 12 during testing) through verification port 40 from HEPA filter 12.

Figure 3:
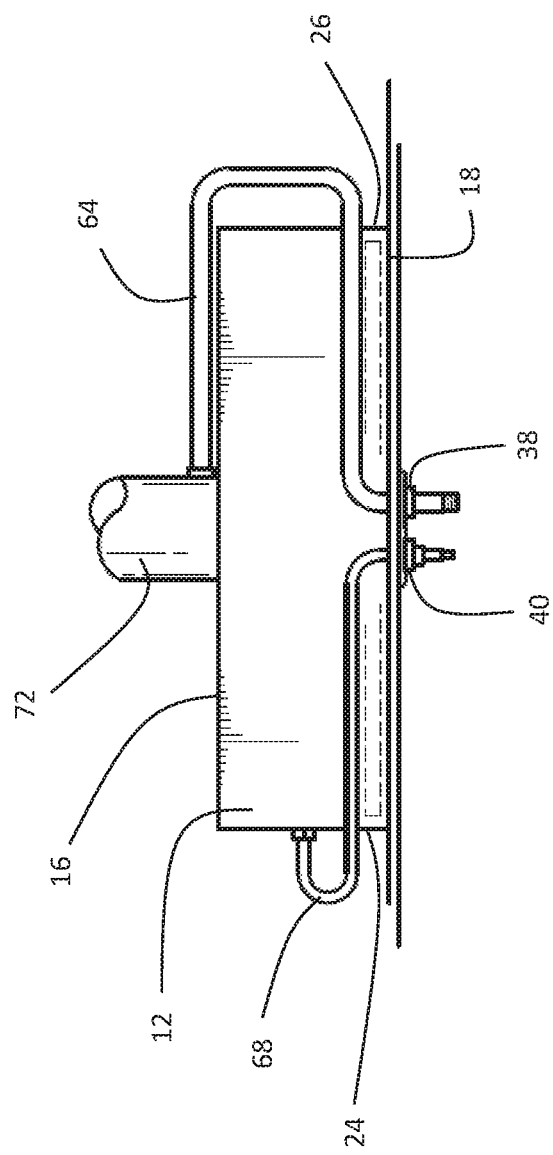
FIG. 3 is a side elevation view of the multi-port system of FIG. 1, showing the HEPA filter disposed above the ceiling and the multi-port system creating a passageway from the sterile room to the filter, in accordance with an embodiment of the present invention.

Referring now to FIG. 3, the connection between multi-port interface 36 and HEPA filter 12 is shown in greater detail. As shown in FIG. 3, HEPA filter 12 includes top surface 16 opposite bottom surface 18, with bottom surface 18 being flush with ceiling 30. Moreover, multi-port interface 36 is flush with ceiling 30. While FIG. 3 depicts HEPA filter 12 and multi-port interface 36 as being flush with ceiling 30, it is appreciated that alternative embodiments may include filter 12 disposed within a room, on a floor of the room, on a sidewall of the room, within a vehicle, within a vacuum or other suction cleaning device, or in other applications that commonly use a HEPA or other filter to trap particles therein. In addition, it is appreciated that multi-port interface 36 may be disposed elsewhere within the sterile room, so long as a secure connection is formed with HEPA filter 12, or may be otherwise disposed external to a HEPA or other filter, depending on the use of the filter.

As shown in FIG. 3, system 10 is in communication with a supply air duct 72, particularly with an air conditioning duct, although it is appreciated that other types of ducts are also contemplated, such as a direct return line or an indirect supply line, such as a branch within a duct. In addition, supply air duct 72 is in communication with HEPA filter 12, such as by air being pumped from duct 72 to the sterile room through filter 12, or by air being removed from the sterile room to duct 72 through filter 12. Regardless, HEPA filter 12 is disposed between the sterile room and supply air duct 72, such that filter 12 can trap contaminants, thereby preventing them from being circulated through the sterile room, such that the sterile room can remain sterile and free of contaminants.

Figure 4:
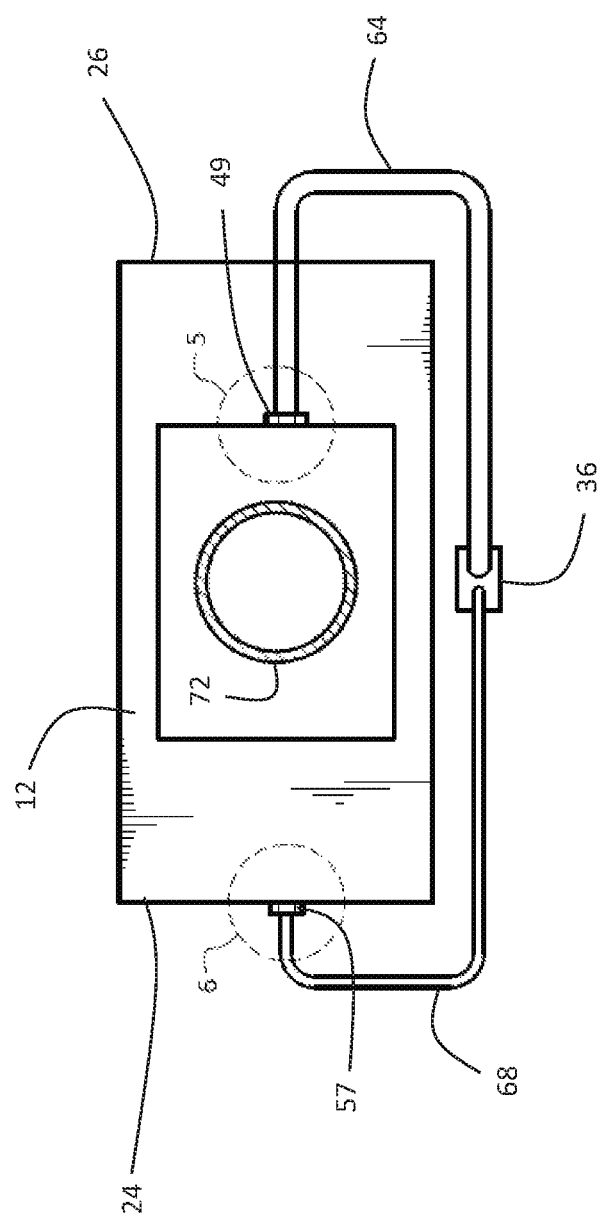
FIG. 4 is a top plan view of the filter test system of FIG. 1, including the multi-port system in communication with the HEPA filter, in accordance with an embodiment of the present invention.

As noted above, system 10 is in communication with supply air duct 72 through multi-port interface 36. Challenge port 38 is connected to supply air duct 72, forming a portion of a closed loop, via challenge line 64. It is preferred that the connection point between challenge line 64 and supply air duct 72 is disposed approximately 6-10 feet above top surface 16 of HEPA filter 12, so that any substances introduced into supply air duct 72 via challenge port 38 has time and space to be thoroughly mixed with the gases already present within supply air duct 72. As such, the concentration of the challenge substances is evenly dispersed within supply air duct 72 prior to interacting with HEPA filter 12. Similarly, verification port 40 is connected to supply air duct 72, forming another portion of the closed loop, via verification line 68. The connection point between verification line 68 and supply air duct 72 is disposed adjacent to bottom surface 18 of HEPA filter 12, such that the verification of the amount of contaminants after traveling through HEPA filter 12 can be accurate and can adequately test HEPA filter 12 for leaks. The attachment points are shown in greater detail in FIG. 4, which also depicts different surfaces of HEPA filter 12, such as left side surface 24 and right side surface 26. While the attachment point between challenge line 64 and supply air duct 72 is shown toward right side surface 26 of HEPA filter 12, it is contemplated that challenge line 64 can be attached toward any side of HEPA filter 12. Similarly, while the attachment point between verification line 68 and HEPA filter 12 is shown on left side surface 24, it is contemplated that verification line 68 can be attached to any side of HEPA filter 12. Moreover, while the attachment between challenge line 64 is shown connected to supply air duct 72, it is contemplated that challenge port 38 can be connected directly to HEPA filter 12, an embodiment that will be discussed in greater detail below.

Figure 5:
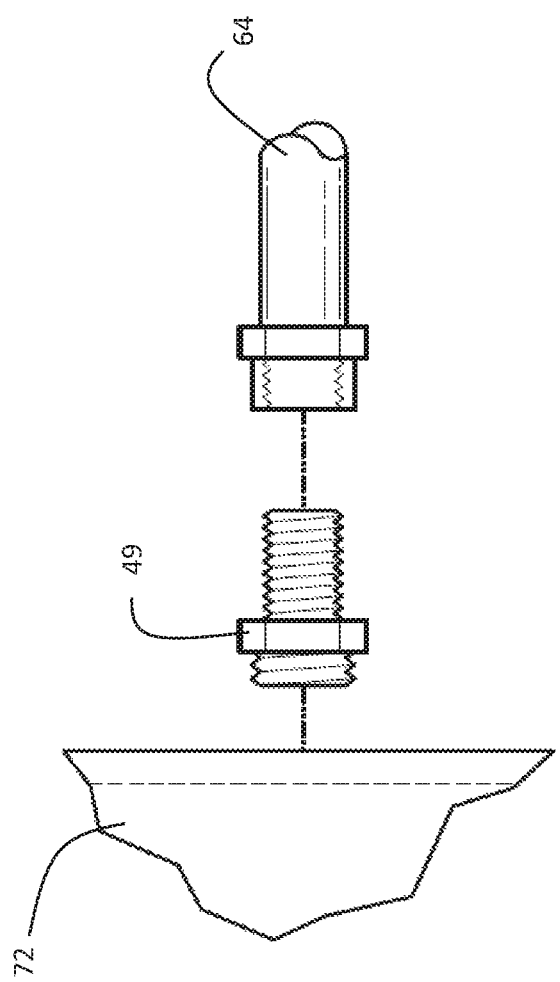
FIG. 5 is a close-up elevation view of the connection shown in FIG. 4 (and circled as numeral 5) between the HEPA filter and a fluidic tube coupled to the challenge port, in accordance with an embodiment of the present invention.
Figure 6:
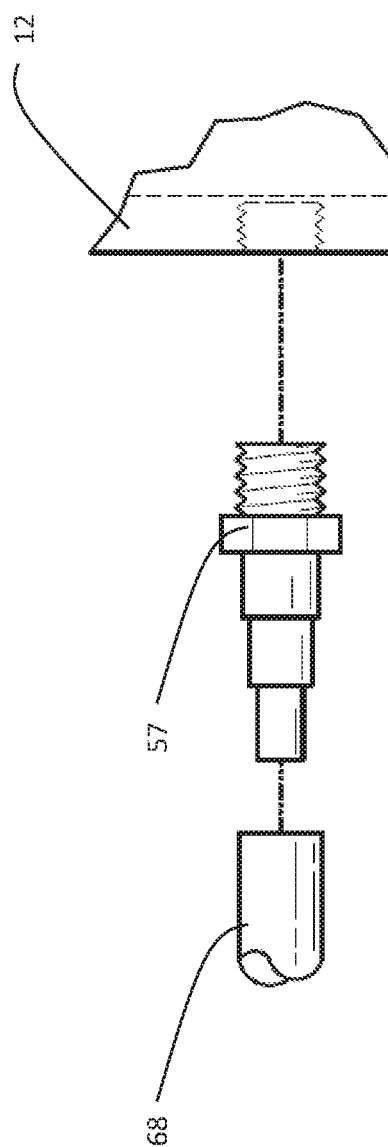
FIG. 6 is a close-up elevation view of the connection shown in FIG. 4 (and circled as numeral 6) between the HEPA filter and a fluidic tube coupled to the verification port, in accordance with an embodiment of the present invention.

FIG. 5 and FIG. 6 depict the attachments between challenge line 64 and supply air duct 72 and between verification line 68 and HEPA filter 12, respectively. As shown in FIG. 5, which depicts the portion of FIG. 4 that is circled and labeled as numeral 5, challenge line 64 is indirectly coupled to supply air duct 72 via challenge fitting 49. Similarly, as shown in FIG. 6, which depicts the portion of FIG. 4 that is circled and labeled as numeral 6, verification line 68 is indirectly coupled to HEPA filter 12 via verification fitting 57. Each of challenge fitting 49 and verification fitting 57 provide secure fittings coupled to each of supply air duct 72 and HEPA filter 12, respectively, such that a closed loop can be created through the entire system 10.

Figure 7:
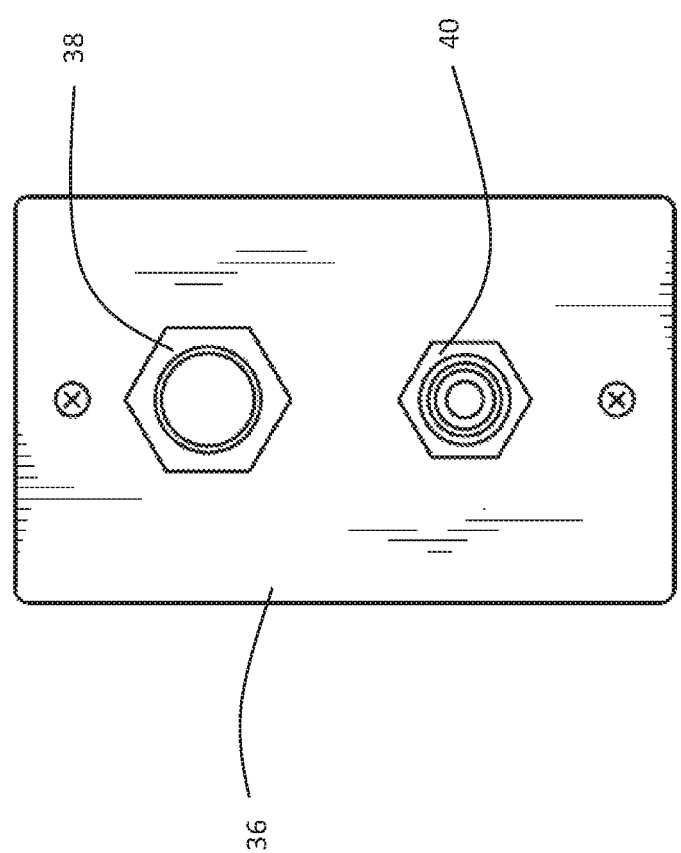
FIG. 7 is a top plan view of the multi-port system of FIG. 1, showing the challenge port and the verification port, in accordance with an embodiment of the present invention.

FIG. 7 depicts a simplified example of multi-port interface 36, including challenge port 38 and verification port 40, with each of the ports being designed to couple with HEPA filter 12. As shown in FIG. 7, challenge port 38 includes a diameter greater than a diameter of verification port 40. The diameter of challenge port 38 is greater to easily allow for the introduction of challenge substances into system 10, since the challenge substances do not need to be pressurized at challenge port 38. The pressurization of challenge substances is discussed in greater detail below. The diameter of verification port 40 is smaller so that a relatively small amount of pressurized air is tested via verification port 40, such that the majority of the air within system 10 flows directly to HEPA filter 12 and not through verification port 40, thereby providing a non-disruptive and accurate sampling of the air via verification port 40.

Figure 8:
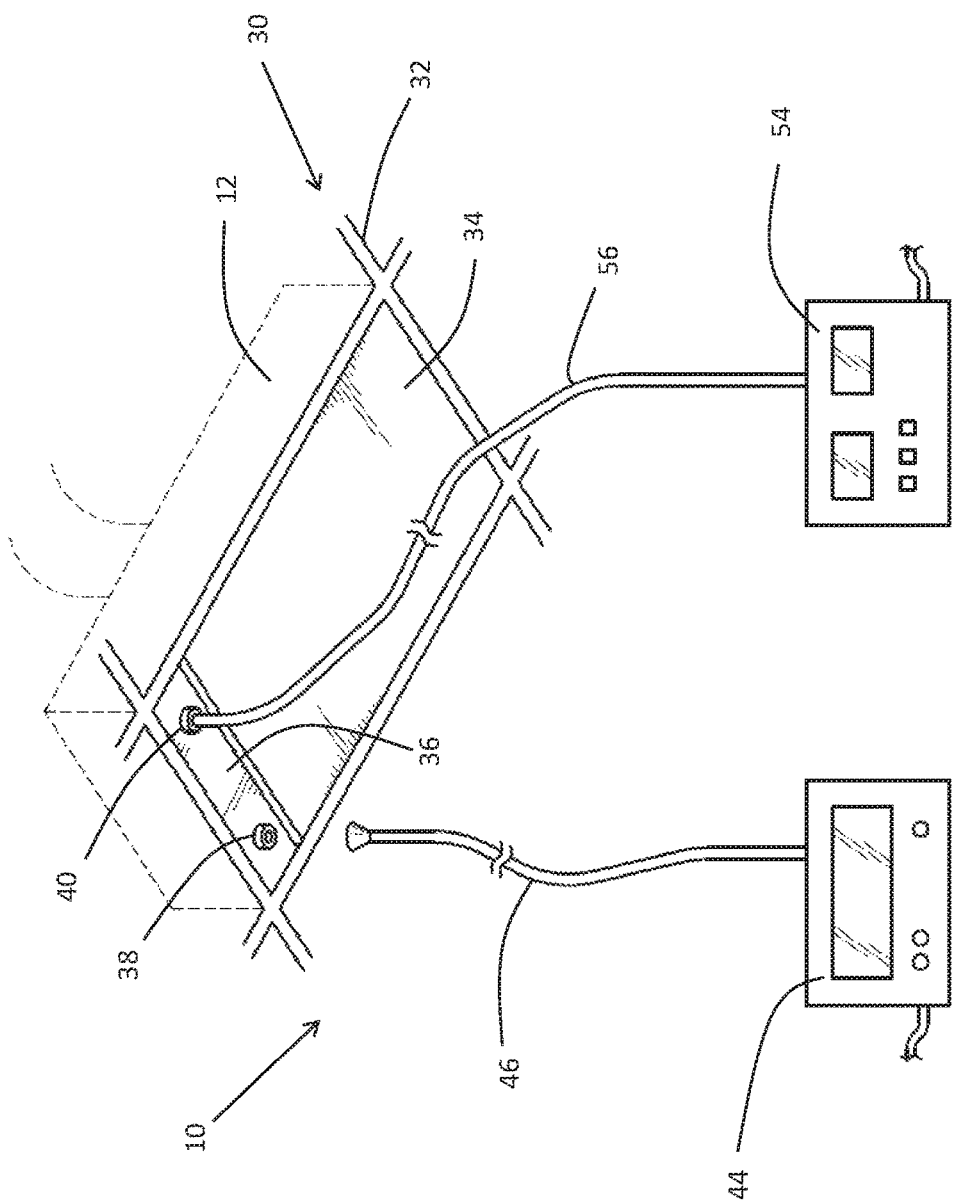
FIG. 8 is a perspective view of a filter test system, including a multi-port system disposed within a ceiling of a sterile room and in communication with a HEPA filter, in accordance with an embodiment of the present invention.

FIG. 8 depicts an alternative embodiment of system 10, including multi-port interface 36 disposed integral with HEPA filter 12, such that multi-port interface 36 is a component of HEPA filter 12. In this embodiment, there is no need to retrofit interface 36 within a sterile room after HEPA filter 12 has already been installed therein. Instead, interface 36 is a component of HEPA filter 12, separate from the filter media but in communication with the air upstream of HEPA filter 12. As such, multi-port interface 36 is easily utilized to test HEPA filter 12 by a technician within the sterile room, without the need to couple interface 36 with HEPA filter 12 after HEPA filter 12 is previously installed within the sterile room.

Figure 9A:
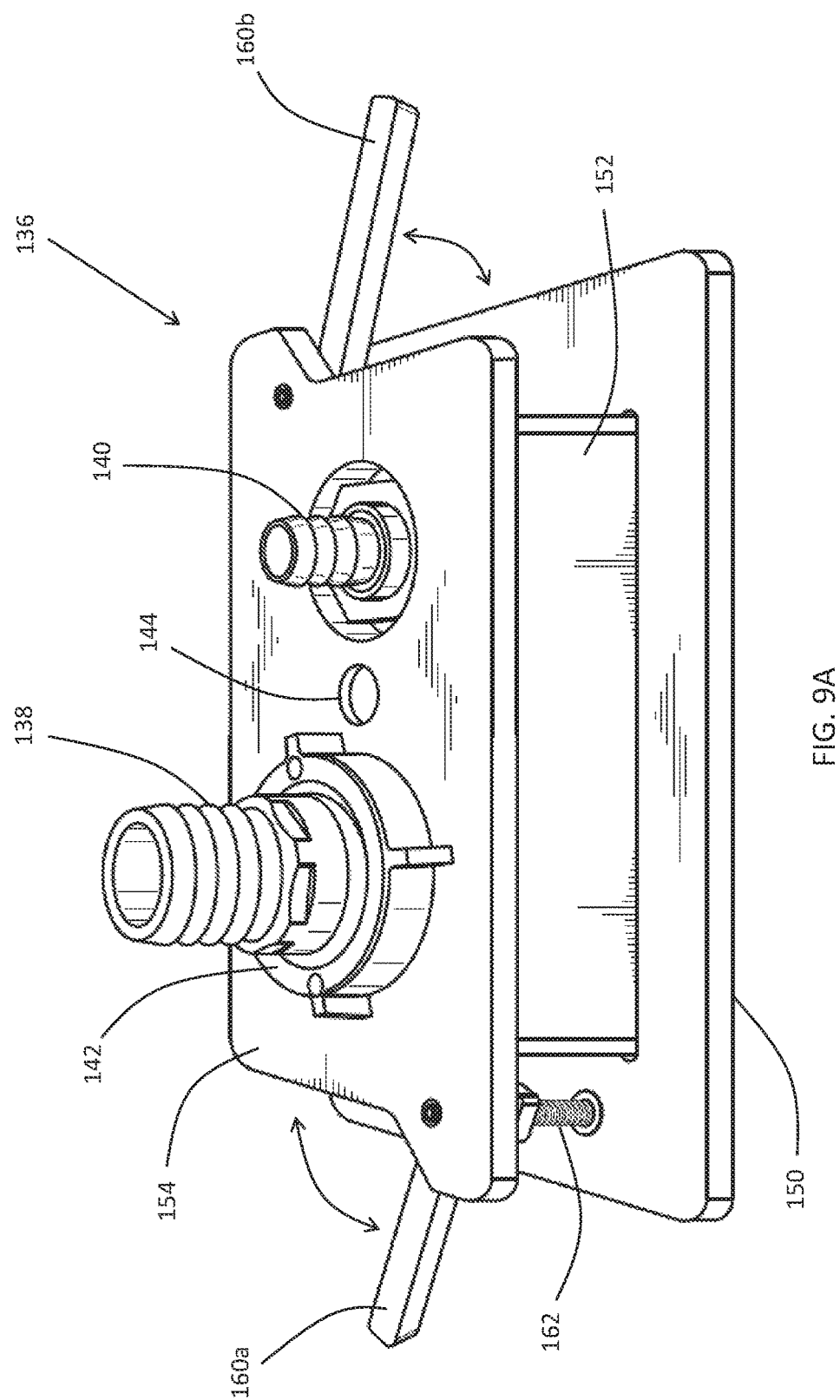
FIG. 9A is a perspective rear view of a multi-port filter test apparatus including a challenge port and a verification port, in accordance with an embodiment of the present invention.
Figure 9B:
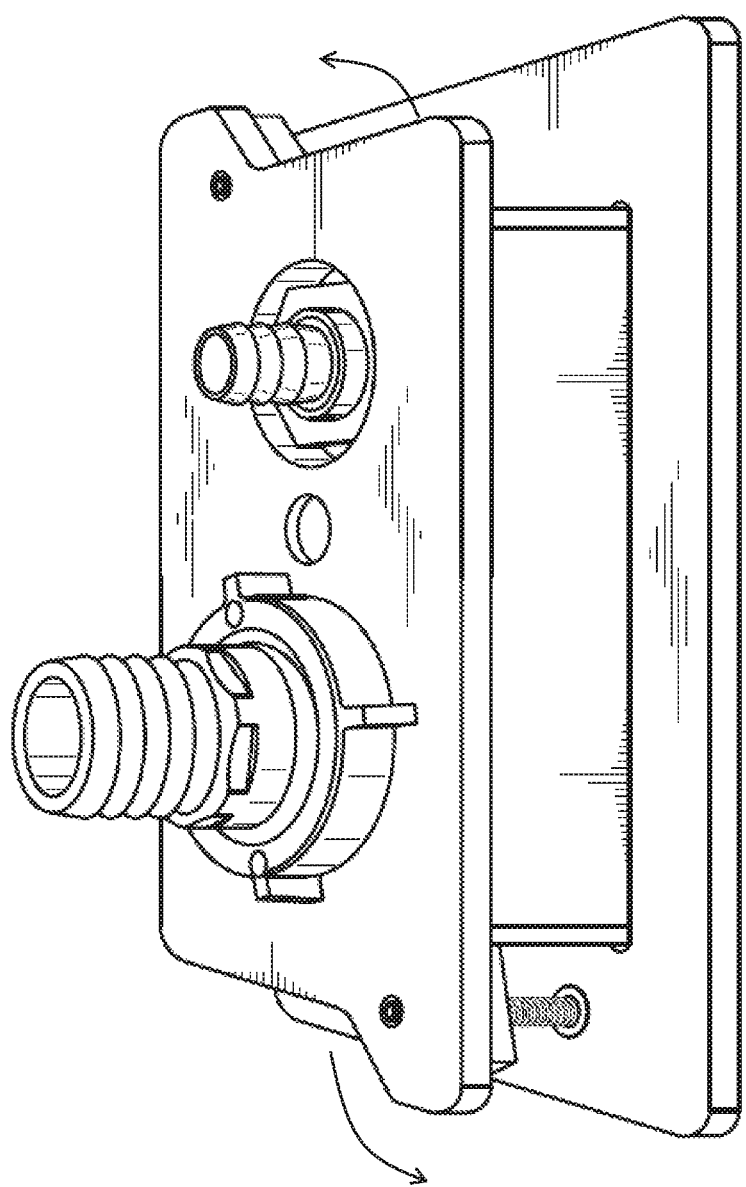
FIG. 9B a perspective rear view of the multi-port filter test apparatus of FIG. 9A, in accordance with an embodiment of the present invention.
Figure 9C:
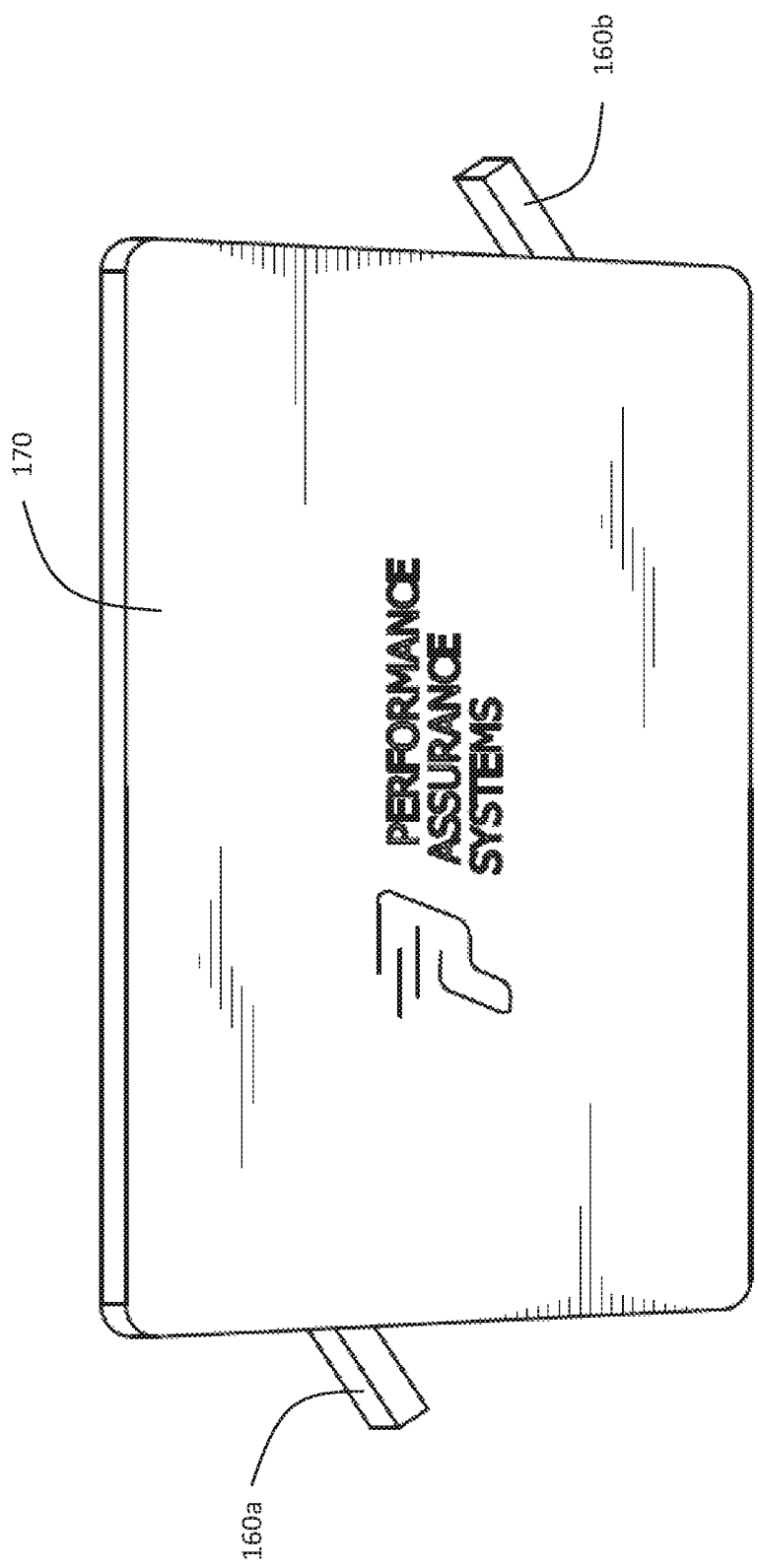
FIG. 9C is a perspective front view of the multi-port filter test apparatus of FIG. 9A, including an aesthetic magnetic cover to conceal the challenge port and verification port, in accordance with an embodiment of the present invention.

FIGS. 9A, 9B, and 9C depict an embodiment of multi-port interface 136, which is similar in many ways to multi-port interface 36. In particular, multi-port interface 136 also includes multiple ports designed to provide attachments between testing equipment and a HEPA filter, creating a closed-loop system between the testing equipment and the HEPA filter through the ports of the interface. Multi-port interface 136 includes challenge port 138 and verification port 140, which are similar to challenge port 38 and verification port 40 discussed in greater detail above. Each of challenge port 138 and verification port 140 provides a through-hole through which testing substances can be introduced into a HEPA filter, and removed from a HEPA filter, respectively. As shown in FIGS. 9A and 9B in particular, the body of challenge port 138 is further secured to multi-port interface 136 via threaded member 142, which is designed to reside adjacent to and flush with back side 154 of interface 136. The sides of interface 136 will be discussed in further detail below.

Multi-port interface 136 is designed to be installed within a ceiling of a room, particularly a sterile room, similar to interface 36 discussed in detail above. Accordingly, multi-port interface 136 includes front side 150 which is adapted to face a sterile room, such that a person within the sterile room would see front side 150 of multi-port interface 136 installed within the ceiling of the sterile room. Multi-port interface 136 also includes back side 154, which is designed to be disposed within the ceiling of the sterile room, toward the HEPA filter. Back side 154 and front side 150 are separated by interface body 152, with the ports of interface 136 extending through body 152 from front side 150 through back side 154. As such, a tube can couple to one of the ports on front side 150 of interface 136, such that fluids can pass through body 152 and back side 154.

To aid in the installation of multi-port interface 136 within a ceiling of a sterile room, interface 136 includes rotatable clips 160a and 160b. Clips 160a and 160b are disposed on back side 154 of interface 136, such that the clips are designed to be disposed within a ceiling, providing an anchor point to further secure interface 136 within the ceiling. Each of clips 160a and 160b is rotatable via screws 162, which extend from front side 150 of interface through back side 154. By rotating screws 162, clips 160a and 160b similarly rotate with respect to multi-port interface 136. As shown in FIG. 9A, clips 160a and 160b can be rotated to extend away from interface 136, thereby providing anchor points when installed in a ceiling. As shown in FIG. 9B, clips 160a and 160b can be rotated to be adjacent to the sides of interface 136 in a storage configuration. The rotation of clips 160a and 160b is depicted by arrows in FIGS. 9A and 9B. Similarly, clips 160a and 160b are shown in an extended configuration in FIG. 9C, which shows cover 170 disposed on front side 150 of multi-port interface 136. Cover 170 provides an aesthetic covering for multi-port interface 136, particularly when interface 136 is not in use, thereby concealing the ports of multi-port interface 136 when the ports are not being used to test a HEPA filter.

Figure 10:
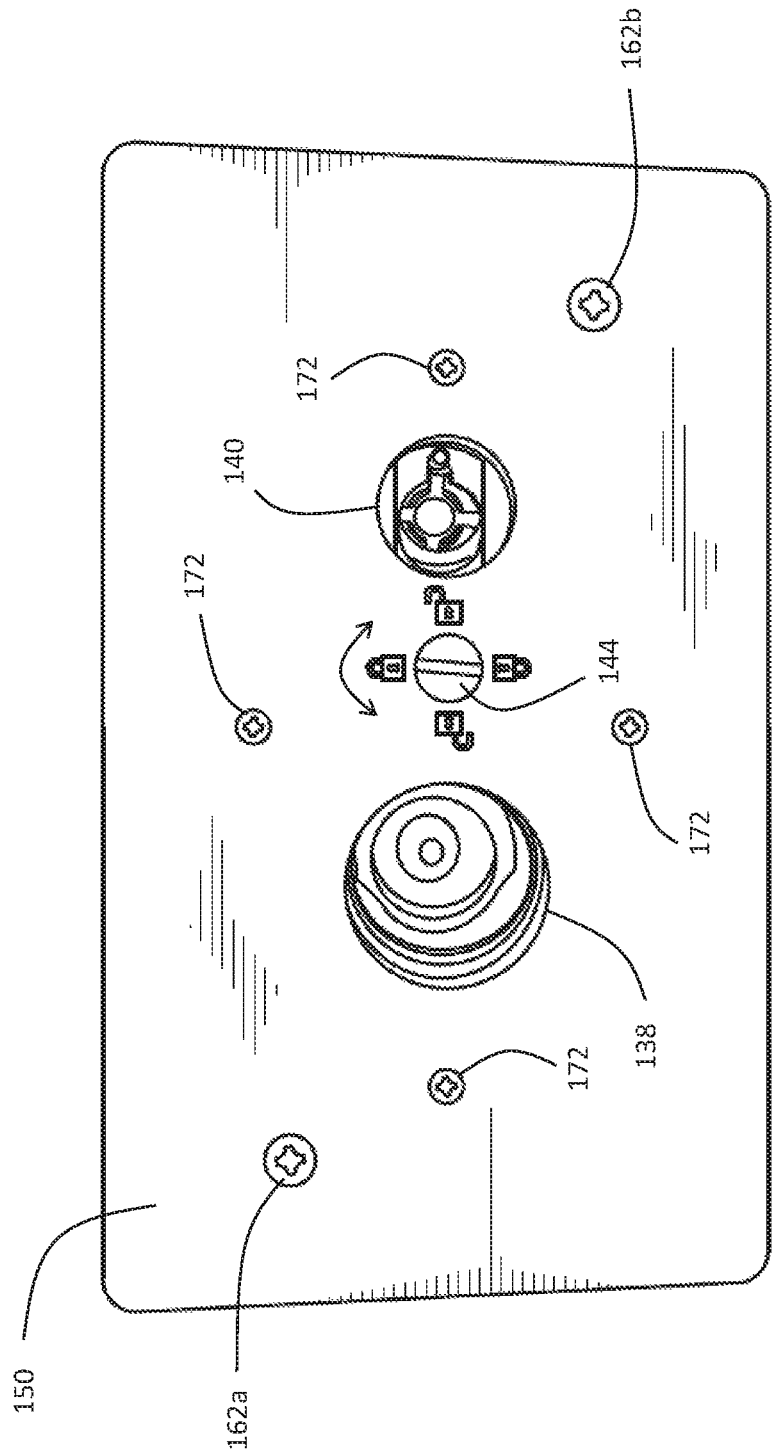
FIG. 10 is a front plan view of the multi-port filter test apparatus of FIG. 9A, showing attachment points for challenge and verification apparatuses, and a cam screw that controls whether the multi-port filter test apparatus is locked or unlocked, in accordance with an embodiment of the present invention.

Turning now to FIG. 10, front side 150 of multi-port interface 136 is shown in greater detail. Front side 150 includes a plurality of metallic components 172, which are disposed about front side 150 to create a magnetic field about front side 150. As such, cover 170 can include oppositely-polarized metallic components to magnetically couple with components 172, thereby securing cover 170 to front side 150 without the need to adhere or otherwise physically secure cover 170 to interface 136. Cover 172 could alternatively be hingedly coupled to front side 150, such that cover 172 can be easily removed to provide access to multi-port interface 136 without the need for external tools to remove cover 172.

Also shown in FIG. 10 are the front sides of screws 162a and 162b, which control the rotation of clips 160a and 160b, respectively. By rotating screws 162a and 162b clockwise and counterclockwise, clips 160a and 160b disposed adjacent to back side 154 are also rotated with respect to multi-port interface 136. Accordingly, clips 160a and 160b can be maneuvered from front side 150 of interface 136, such that the clips can be installed against and removed from a ceiling from a sterile room, without the need to gain direct access to the space above a ceiling to install and remove interface 136 within the sterile room.

As shown in FIG. 10, multi-port interface 136 also includes cam screw 144, which is rotatable with respect to interface 136. The rotation of cam screw 144 controls a locking mechanism within each of challenge port 138 and verification port 140, thereby allowing for the connection and removal of tubes coupled to each of the ports. The internal mechanisms of multi-port interface 136 will be described in greater detail below.

Figure 11A:
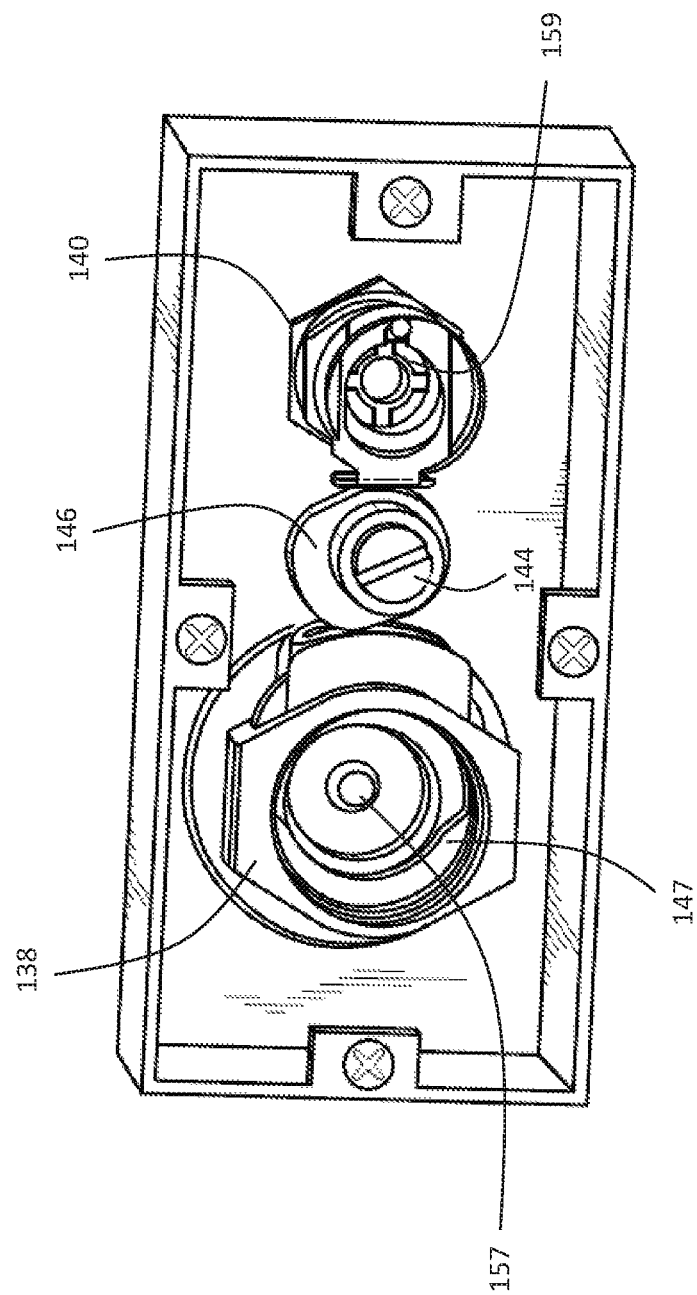
FIG. 11A is an internal front perspective view of the multi-port filter test apparatus of FIG. 9A, showing the effect of turning the cam screw counterclockwise to unlock the challenge port, allowing for the removal of a challenge line coupled to the challenge port, in accordance with an embodiment of the present invention.
Figure 11B:
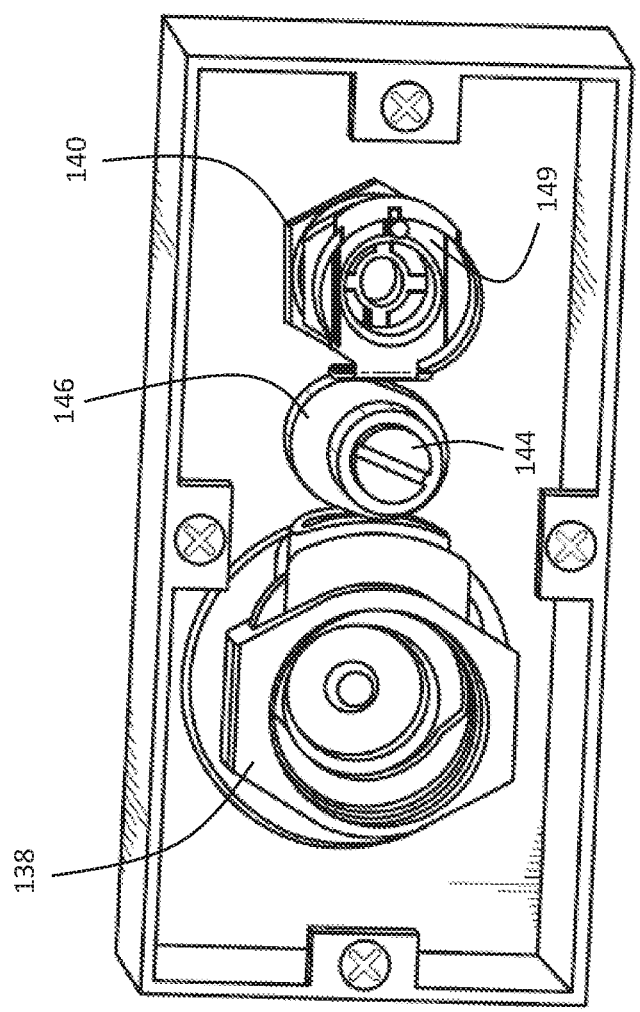
FIG. 11B is an internal front perspective view of the multi-port filter test apparatus of FIG. 9A, showing the effect of turning the cam screw clockwise to unlock the verification port, allowing for the removal of a verification line coupled to the verification port, in accordance with an embodiment of the present invention.

Turning now to FIGS. 11A and 11B, the internal components of multi-port interface 136 are shown in greater detail. As discussed above, cam screw 144 is rotatable with respect to multi-port interface 136. Cam screw 144 is coupled to actuator 146, which is an extension that is designed to rotate and overcome a spring force on one of challenge port 138 and verification port 140, thereby unlocking one of the ports to provide for adding or removing a tube from the port. For example, as shown in FIG. 11A, challenge port 138 includes spring-loaded component 147 that is biased to be disposed within the aperture of challenge port 138 in a locked configuration. In the locked configuration, a tube coupled to challenge port 138 is secured within the aperture of challenge port by spring-loaded component 147, and cannot be safely removed without overcoming the biasing force of spring-loaded component 147 and thereby translating spring-loaded component 147 away from the aperture. As such, when cam screw 144 rotates counterclockwise with respect to interface 136, actuator 146 also rotates and exerts a force on spring-loaded component 147 of challenge port 138. When cam screw 144 rotates approximately 90° counterclockwise, actuator 146 is approximately horizontal with respect to front side 150 of interface 136. When actuator 146 is approximately horizontal, cam screw 144 is in an unlocked configuration, and spring-loaded component 147 is translated away from the aperture of challenge port 138. As such, a tube coupled to challenge port 138 is no longer secured in place by spring-loaded component 147, and the tube can be removed from challenge port 138. FIG. 11B shows the rotation of cam screw 144 toward verification port 140, such that spring-loaded component 149 is translated away from the aperture of verification port 140 if cam screw 144 and actuator 146 rotate approximately 90° clockwise to be approximately horizontal with respect to front side 150 of interface 136. The mechanism of overcoming the biasing force of spring-loaded component 149 is largely identical to that of spring-loaded component 147, and a tube coupled to verification port 140 is similarly safely removed only by rotating cam screw 144 to unlock verification port 140.

Also shown in FIG. 11A in particular are the valve actuators within each of challenge port 138 and verification port 140. Each of the ports has a default configuration that is closed to air flow—in other words, even when equipment is connected to the ports, unless the valves are actuated and allow for air flow, the system is closed to air flow, unless the valves are actuated by an insert. When an input line secures within each of the ports, however, and when it is desired that air flow through multi-port interface 136, the valves are actuated to allow for the air flow. As shown in FIG. 11A, challenge port 138 includes valve 157 disposed within the aperture of challenge port 138. Valve 157 prevents air flow through challenge port 138, unless valve 157 is actuated by an input line translating valve 157 toward back side 154 of interface 136. Similarly, verification port 140 includes valve 159 disposed within the aperture of verification port 140. Similar to valve 157, valve 159 prevents air flow through verification port 140, unless valve 159 is actuated by an output line translating valve 159 toward back side 154 of interface 136. The valve actuation mechanism described above is an example of a valve actuator; it is contemplated that other methods of actuation may be possible, such as translations of valves 157 and 159 toward front side 150 of interface 136. Moreover, a singular valve may take the place of valves 157 and 159, with the singular valve being independently actuated to allow for air flow through the system.

Figure 12A:
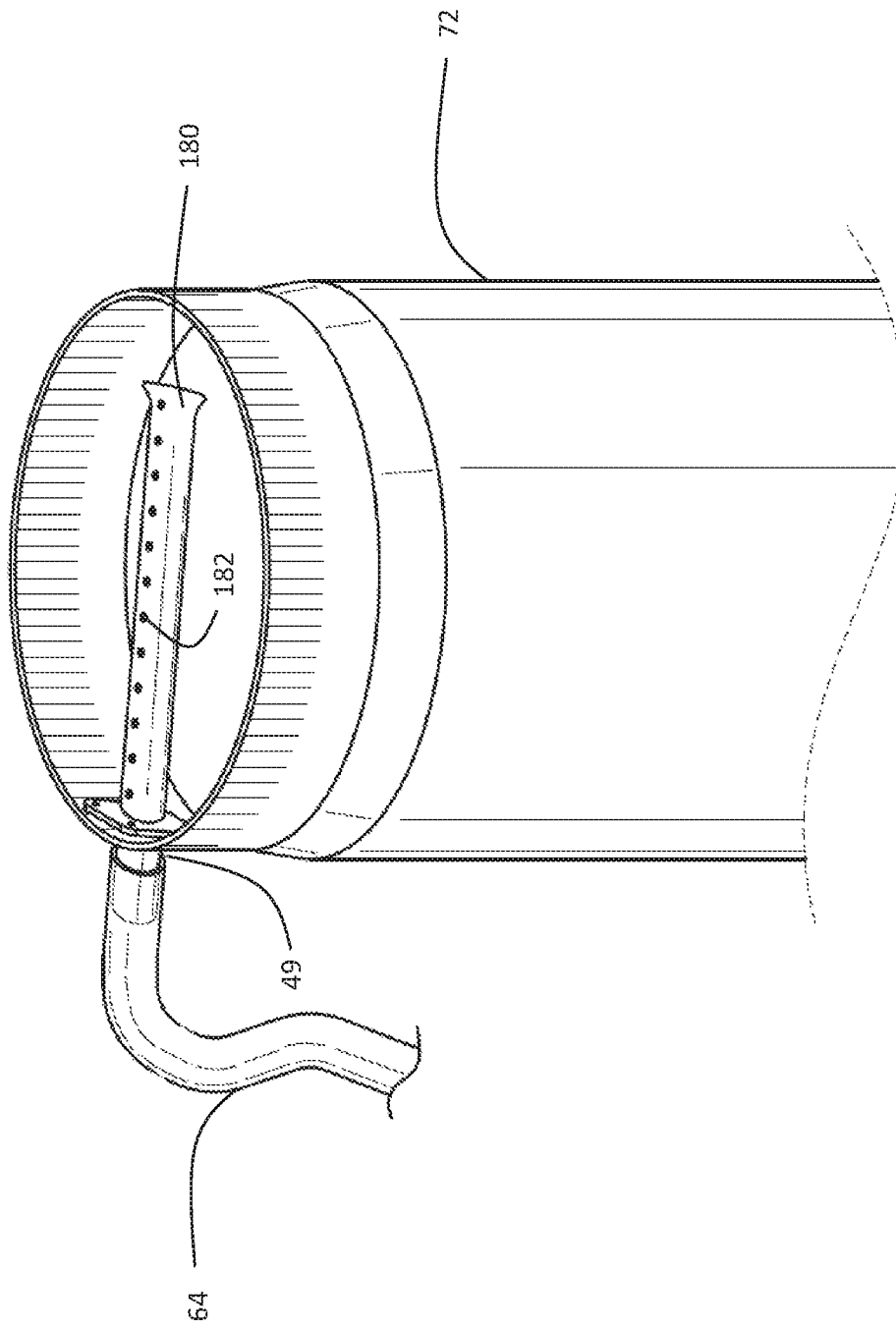
FIG. 12A is a perspective view of an embodiment of a dispersal pipe disposed within an air conditioning duct upstream of a HEPA filter, the dispersal pipe indirectly coupled to the challenge port to introduce testing substances from the challenge port upstream of the HEPA filter, in accordance with an embodiment of the present invention.

Turning now to FIGS. 12A and 12B, embodiments of dispersal pipes are shown in greater detail. As discussed above, it is important that any testing substances introduced into system 10 are introduced above the HEPA filter 12 media to allow the testing substances to mix with the air already present in the system. As such, an embodiment of the present invention includes a dispersal pipe designed to disperse the testing substances throughout the system to sufficiently mix the substances with the air in the system. As such, the dispersal pipe is in communication with challenge port 138, particularly via first intermediate line 64 from challenge port 138 to the system, and coupled to the system via primary filter fitting 49.

As shown in FIG. 12A in particular, an embodiment of a dispersal pipe is shown as straight pipe 180. Straight pipe 180 includes a plurality of apertures 182 that are spaced about the surfaces of straight pipe 180, such that the testing substances introduced into the system via challenge port 138 are relatively evenly dispersed throughout the system via apertures 182. In the absence of dispersal pipe, the testing substances would simply be introduced into the system by traveling through primary filter fitting 49 and would be concentrated in the area immediately surrounding fitting 49. As such, it is unlikely that such a system would create a relatively uniform concentration of the testing substances within the system, and would likely result in an inaccurate test result (i.e., showing a concentration either too high or too low, depending on where the sample is taken from and whether the testing substances dispersed properly). Instead, straight pipe 180 with the plurality of apertures 182 allows for testing substances to be dispersed throughout the system, leading to a higher likelihood that the testing substances will disperse through the system and thereby provide an accurate testing result. The combined diameter of each of the plurality of apertures 182 is preferably equal to the diameter of first intermediate line 64, such that there is no different in pressure within dispersal pipe 180 when the testing substances enter the pipe at fitting 49.

FIG. 12B depicts an embodiment of the dispersal pipe, denoted as coiled pipe 190, similarly including a plurality of apertures 192, similar to straight pipe 180 described in detail above. The difference between coiled pipe 190 and straight pipe 180 is that coiled pipe 190 includes a greater surface area which may include branches from the main intake portion of the pipe. Due to the greater surface area and the branches through which the testing substance can traverse before entering into the system, the amount of testing substance injected into the system is highly controlled and spread out. As a result, the embodiment of dispersal pipe 190 shown in FIG. 12B can be integrated directly into a HEPA filter, and does not need to be installed several feet above the HEPA filter, since the dispersal of gases through pipe 190 is much more spread out and less likely to result in a high concentration of gas in one particular area of the HEPA filter.

Figure 13:
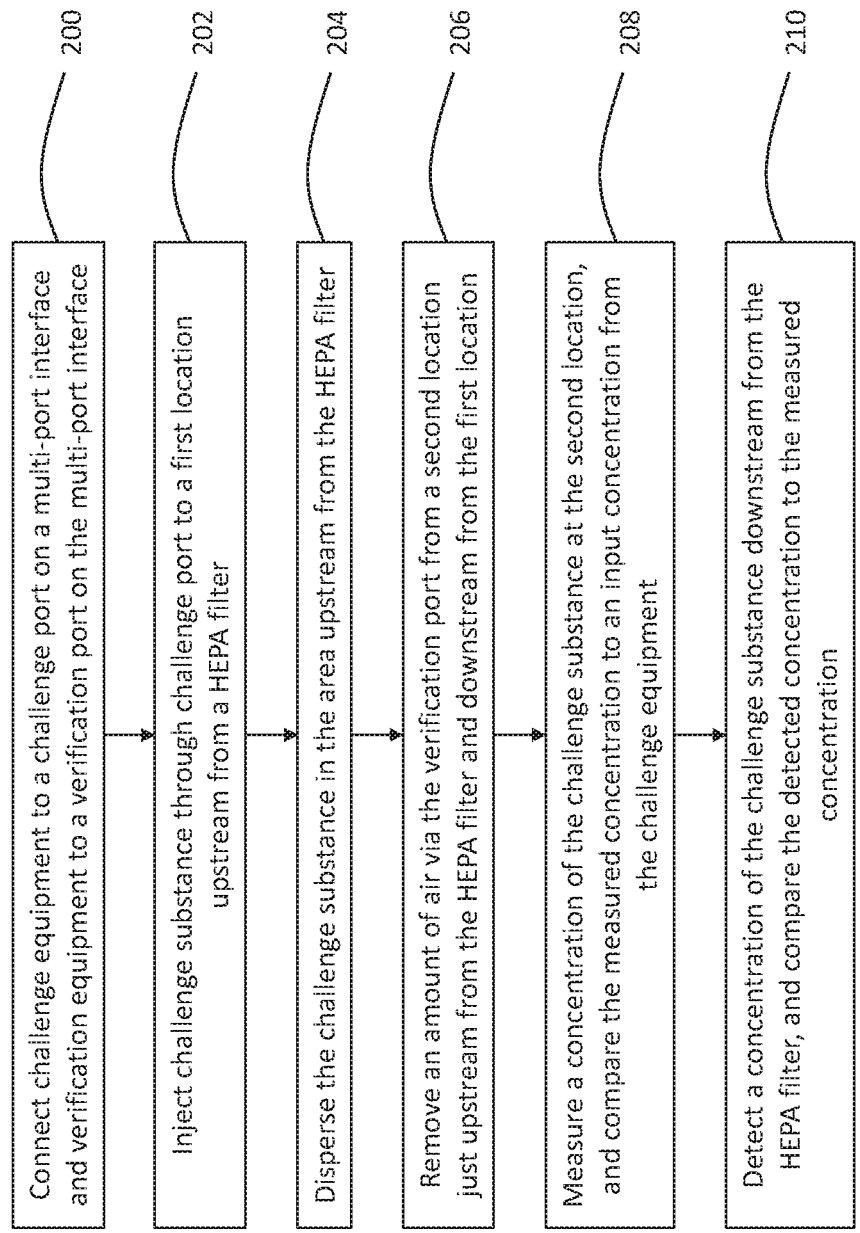
FIG. 13 is a process-flow diagram depicting a method of testing a HEPA filter, in accordance with an embodiment of the present invention.

Referring now to FIG. 13, in conjunction with FIGS. 1-12B, an exemplary process-flow diagram is provided, describing a method of accurately testing a HEPA filter by using a multi-port interface. The steps delineated in the exemplary process-flow diagram of FIG. 13 are merely exemplary of a preferred order of accurately testing a HEPA filter, and the steps may be carried out in another order, with or without additional steps included therein.

The method begins at step 200, during which challenge equipment is connected to a multi-port interface via a challenge port, and verification equipment is connected to the multiport interface via a verification port. When the challenge equipment and the verification equipment are connected to the multi-port interface, each of the equipment is secured within the ports of the multi-port interface, such as through a spring-loaded mechanism described above. Alternatively, the equipment may be threaded into the interface, screwthreadedly-connected to the interface, adhered to the interface, coupled via a magnetic relationship, or via other similar securing mechanisms known in the art. Moreover, in order to disconnect the equipment from the interface, an actuator must be utilized to allow for the disconnection—for example, a spring must receive a force from an actuator to compress and allow for disconnection of the equipment.

In a default configuration, each of the challenge port and the verification port is closed to the exterior environment. As such, gas can only flow through the multi-port interface by interacting with one or both of the challenge equipment and the verification equipment. The flow of gas in controlled within each of the apertures of the challenge port and the verification port, with gas only being allowed to flow by actuating a valve within the ports. Typically, the valves are actuated by input lines coupled to the ports, which function to change the configuration of the ports to be open to gas flow.

When the challenge equipment is connected to the challenge port of the multi-port interface, the method proceeds to step 202, during which a challenge substance is injected through the challenge port. The challenge substance is introduced into an area upstream from a HEPA filter during step 204. In an embodiment, the challenge substance is introduced between 6 and 10 feet above the HEPA filter to allow the substance to disperse within the air upstream from the HEPA filter, thereby ensuring that an accurate reading of the concentration of challenge substance is calculated later in the method. The challenge substance is typically an aerosol substance that is designed to test the efficiency of a HEPA filter, with the challenge substance designed to be dispersed toward the HEPA filter and retained by the filter media within the HEPA filter. If more than a threshold value of the challenge substance is detected downstream from the HEPA filter, then there is likely a leak in the HEPA filter, and the filter should be replaced. The calculation is discussed in greater detail below.

The method next proceeds to step 206, during which an amount of the air in the area just upstream from the HEPA filter is removed from the system via the verification port discussed above. The air is drawn through the verification port by the verification equipment, which is designed to test a concentration of the challenge substance within the air sample removed from the system. Since the challenge equipment and the verification equipment work in tandem, a technician or machine can compare the concentration injected into the system (as indicated by the challenge equipment) with the concentration measured by the verification equipment during step 208. As such, the verification equipment provides an accurate representation of the concentration of the challenge substance within the system, since the concentration is compared with the injected concentration before performing a final calculation on the status of the HEPA filter.

After the verification equipment obtains a calculation of the concentration of the challenge substance, the method proceeds to step 210, during which a technician or machine disposed within a sterile room downstream from the HEPA filter obtains a reading of the concentration of the challenge substance detected in the sterile room. As such, the technician measures the amount (if any) of the challenge substance that entered into the sterile room and that was not captured by the HEPA filter. The concentration detected within the sterile room is compared with the concentration of challenge substance measured during step 208, and a final calculation is performed to determine the if the HEPA filter should be replaced. The HEPA filter should be replaced if the concentration detected in step 210 is above a threshold value, such as 0.01 micrograms of the challenge substance per Liter of air. However, it is appreciated that different challenge substances may result in different threshold values, and that different HEPA filters may result in different threshold values.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A testing system for use in combination with a high efficiency particulate air (HEPA) filter, the testing system comprising:
   a multi-port interface including a challenge port independent from a verification port, the challenge port defining an aperture through which a challenge substance can be injected, and the verification port defining an aperture through which an amount of the challenge substance can be removed for testing, the challenge substance adapted to test a status of the HEPA filter;
   a first intermediate line secured to the challenge port at a first end and to a supply air duct in communication with the HEPA filter at a second end, the second end being disposed upstream from the HEPA filter such that the concentration of the challenge substance disperses through an area upstream from the HEPA filter, the supply air duct adapted to translate airflow toward the HEPA filter; and
   a second intermediate line secured to the verification port at a first end and to the supply air duct at the second end, the second end being disposed between a bottom surface of the HEPA filter and the second end of the first intermediate line, such that an amount of air can be removed from the system via the second intermediate line, the amount of air adapted to be tested for the concentration of the challenge substance, such that an accurate test can be performed on leakages within the HEPA filter.

2. The testing system of claim 1, wherein the challenge port further comprises a valve extending toward the aperture, the valve adapted to control the flow of the challenge substance through the challenge port.

3. The testing system of claim 1, wherein the verification port further comprises a valve extending toward the aperture, the valve adapted to control the flow of the amount of air through the verification port.

4. The testing system of claim 1, further comprising a dispersal pipe coupled to the second end of the first intermediate line, the dispersal pipe disposed within the area of the supply air duct disposed upstream from the HEPA filter and adapted to disperse the challenge substance throughout the area to mix the challenge substance with the air within the area.

5. The testing system of claim 4, wherein the dispersal pipe includes a plurality of apertures designed to evenly disperse the challenge substance within the area of the supply air duct disposed upstream from the HEPA filter.

6. The testing system of claim 5, wherein a collective diameter of the plurality of apertures is equal to a diameter of the first intermediate line, thereby reducing a risk of impaction associated with differences in pressure.

7. The testing system of claim 1, further comprising a magnetic cover removably affixed to a front surface of the multi-port interface, such that the multi-port interface can be concealed when not in use.

8. The testing system of claim 1, further comprising a cam screw in communication with the challenge port, the cam screw adapted to apply a force against a spring-loaded component to compress the spring-loaded component, such that an input line can be inserted and removed from the challenge port.

9. The testing system of claim 1, further comprising a cam screw in communication with the verification port, the cam screw adapted to apply a force against a spring-loaded component to compress the spring-loaded component, such that an output line can be inserted and removed from the verification port.

10. The testing system of claim 1, further comprising one or more rotatable clips each secured to the multi-port interface via a screw, each of the one or more rotatable clips rotatable with respect to the multi-port interface, such that the clips are installable within a ceiling panel proximate to the HEPA filter.

* * * * *